United States Patent [19]

Forestier et al.

[11] Patent Number: 5,223,249
[45] Date of Patent: Jun. 29, 1993

[54] COSMETIC COMPOSITION AND METHODS CONTAINING DIORGANOPOLY-SILOXANES CONTAINING A 2-HYDROXYBENZOHENONE GROUP

[75] Inventors: Serge Forestier, Claye-Souilly; Gerard Lang, Saint-Gratien; Herve Richard, Paris, all of France

[73] Assignee: L'Oreal, Paris, France

[21] Appl. No.: 497,262

[22] Filed: Mar. 22, 1990

[30] Foreign Application Priority Data

Mar. 22, 1989 [FR] France ................................ 8903783

[51] Int. Cl.⁵ .................. A61K 7/42; A61K 7/44; A61K 7/48; A61K 9/12
[52] U.S. Cl. .................... 424/59; 424/DIG. 5; 424/47; 424/60; 424/63; 424/70; 514/844; 514/847; 514/938; 514/964
[58] Field of Search ............................ 424/59, 60, 47

[56] References Cited

U.S. PATENT DOCUMENTS

| | | | |
|---|---|---|---|
| 2,833,802 | 5/1958 | Merker | 424/59 X |
| 2,929,829 | 3/1960 | Morehouse | 424/59 X |
| 2,938,047 | 5/1960 | Black | 424/59 X |
| 3,185,627 | 5/1965 | Kass | 424/59 X |
| 3,296,196 | 1/1967 | Lamoreaux | 424/59 X |
| 4,278,804 | 7/1981 | Ashby et al. | 556/436 |
| 4,696,969 | 9/1987 | Thimineur et al. | 524/762 |

FOREIGN PATENT DOCUMENTS

| | | | |
|---|---|---|---|
| 0138590 | 4/1985 | European Pat. Off. | 424/59 |
| 1518231 | 6/1967 | France | 424/59 |

OTHER PUBLICATIONS

*Chemical Abstracts*, vol. 103, No. 22, Dec. 1985, p. 343, No. 183382p.
*Die Makromolekulare Chemie*, vol. 188, No. 11, Nov., 1987 pp. 2759-2767, Basel, Switzerland; Nestor et al.

Primary Examiner—Dale R. Ore
Attorney, Agent, or Firm—Marshall, O'Toole, Gerstein, Murray & Borun

[57] ABSTRACT

Use in cosmetics, especially as UV screens, of diorganopolysiloxanes containing a 2-hydroxybenzophenone functional group of formula:

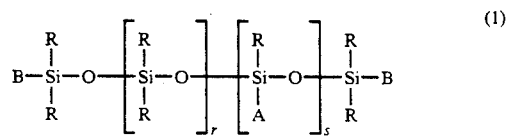

(1)

where R is $C_1$-$C_{10}$ alkyl, phenyl or 3,3,3-trifluoropropyl, B is R or A, r=0-200, s=0-50, or of formula:

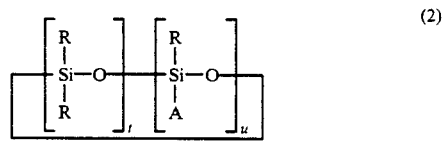

(2)

where u=1-20 and t=0-20 and t+u≧3, A and/or B denoting a 4-alkyleneoxy-2-hydroxybenzophenone radical.

12 Claims, No Drawings

COSMETIC COMPOSITION AND METHODS CONTAINING DIORGANOPOLY-SILOXANES CONTAINING A 2-HYDROXYBENZOHENONE GROUP

The present invention relates to the use of diorganopolysiloxanes containing a 2-hydroxybenzophenone functional group in cosmetics, especially as agents screening UV radiation, and to new cosmetics compositions containing these compounds, intended for protecting skin and hair.

It is known that light radiations of wavelengths between 280 nm and 400 nm allow human skin to tan and that rays of wavelengths between 280 and 320 nm, known by the name of UV-E, produce erythemas and skin burns which can be detrimental to the development of the tan; this UV-B radiation must therefore be screened out.

It is also known that UV-A rays, of wavelengths between 320 and 400 nm, causing skin to tan, are capable of inducing a change in the latter, especially in the case of a sensitive skin or a skin which is continually exposed to solar radiation. In particular, UV-A rays give rise to a loss of elasticity of the skin and the appearance of wrinkles, leading to premature aging. They promote the triggering of the erythematous reaction or intensify this reaction in some individuals and can even be at the source of phototoxic or photoallergic reactions.

It is therefore advantageous to have available compounds which absorb UV rays over a broad band, in order to be able to filter out both UV-A and UV-B rays.

It is known, furthermore, that light attacks the keratin in hair. Many publications disclose that natural light destroys certain amino acids in hair and that, by modifying the capillary fibre, it decreases its mechanical properties; this decrease in the mechanical properties can be revealed as the decrease in the 15% elongation plateau for wet hair or as the increase in alkaline solubility.

The plateau at 15% elongation is the weight which must be applied to a wet hair of a given length to lengthen it by 15%. The greater the weight, the more elastic and resistant the hair.

The alkaline solubility makes it possible to evaluate the degradation of the polypeptide chains of the hair by determining the protein matter dissolved in an alkaline solution.

The higher the alkaline solubility, the more the hair is changed and degraded.

It is therefore desirable to provide hair with good protection against photochemical degradation in order to preserve its mechanical properties and to avoid its bleaching or changing colour.

It is also known that the constituents forming part of cosmetic preparations do not always have a sufficient stability to light and that they are degraded under the effect of light radiations.

Consequently, it is desirable to incorporate in these preparations compounds capable of filtering out UV rays and which must additionally exhibit a good stability and a sufficient solubility in the media usually employed in cosmetics, and in particular in oils and fats.

It is known, moreover, to graft residues of molecules which have a filtering effect on UV radiation onto synthetic carbonaceous polymer chains, onto natural polymers like proteins or protein hydrolysates or else onto polyaminoamides; these graft polymers, described, for example, in French Pat. Nos. 2,197,023, 2,237,912, 2,531,960, 2,548,018, 2,549,069, 2,586,692 and 2,586,693, can be employed for preparing sunscreen or cosmetic compositions for protecting the human skin. It has been found, however, that these graft polymers are generally poorly soluble in the usual cosmetic solvents, especially in fatty substrates, and that they form films whose structure is too rigid.

Now, the Applicant has found that certain diorganopolysiloxanes containing a 2-hydroxybenzophenone functional group exhibit, astonishingly, good cosmetic properties in combination with good screening properties over a wide region of wavelengths ranging from 280 to 360 nm. In particular, they exhibit an excellent liposoluble character, which enables them to be employed in the fatty substrates employed in cosmetics. In addition to their good screening power and their good solubility in fatty substances and the usual cosmetic solvents, these diorganopolysiloxanes containing a 2-hydroxybenzophenone functional group exhibit an excellent chemical and photochemical stability and are tolerated well by the skin and the hair, which they endow with softness.

In addition, they have the advantage of preserving the mechanical properties and the colour of hair against degradation by light. It has been possible to demonstrate this advantage on exposure in natural light (sunny environment), and in artificial light (xenon source in an accelerated aging apparatus of the Hanau Suntest type).

The subject of the present invention is therefore the use in cosmetics, as agents screening out the UV radiation of wavelengths between 280 and 360 nm, of diorganopolysiloxanes containing a 2-hydroxybenzophenone functional group, which are chosen from those of formula:

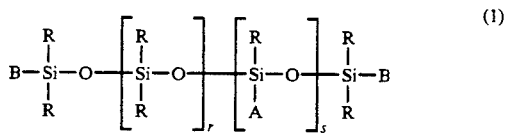

(1)

in which the symbols:
R, which are identical or different, are chosen from linear or branched $C_1$–$C_{10}$ alkyl, phenyl and 3,3,3-trifluoropropyl radicals, at least 80% of the number of the radicals R being methyl radicals,
B, which are identical or different, are chosen from the radicals R and the radical A,
r is a number chosen between 0 and 200 inclusive,
s is a number chosen between 0 and 50 inclusive
and, if s is 0, at least one of the two symbols B denotes A,
and those of formula:

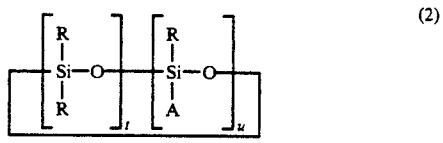

(2)

in which
R has the same meaning as in formula (1),
u is a number between 1 and 20 inclusive, and
t is a number between 0 and 20 inclusive,
the sum (t+u) is equal to or greater than 3, in which formulae the symbol A is a radical of formula:

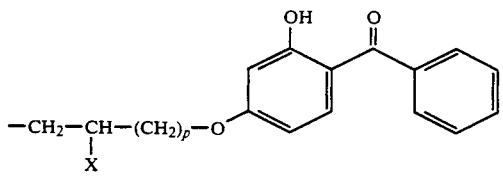

in which:
X is a hydrogen atom or a linear or branched $C_1$-$C_4$ alkyl radical, and
p is an integer between 1 and 10 inclusive.

More particularly, random or block polymers of formulae (1) or (2) exhibiting at least one of the following characteristics are employed:
R is methyl,
B is methyl,
r is between 5 and 20 inclusive,
s is between 2 and 15 inclusive,
t+u is between 3 and 10 inclusive,
p=1,
X=H or methyl.

To prepare the polymers of formulae (1) and (2) it is possible, for example, to start with the corresponding polymer in which all the radicals A are hydrogen atoms.

This polymer is called SiH-containing polymer in what follows; the SiH groups may be present in the chain and/or at the chain ends. These SiH-containing polymers are products which are well known in the silicones industry and are generally available commercially.

They are described, for example, in U.S. Pat. Nos. 3,220,972, 3,436,366, 3,697,473 and 4,340,709.

This SiH-containing polymer may therefore be chosen from those of formula:

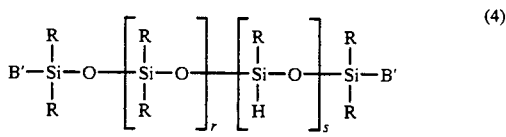

in which R, r and s have the meaning given above for formula (1) and the radicals B', which are identical or different, are chosen from the radicals R and a hydrogen atom, and of formula:

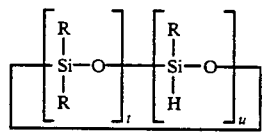

in which R, t and u have the meaning given above for formula (2).

A hydrosilylation reaction is performed with the aid of this SiH-containing polymer of formula (4) or (5), in the presence of a catalytically effective quantity of a platinum catalyst, with an organic 2-hydroxybenzophenone derivative of formula:

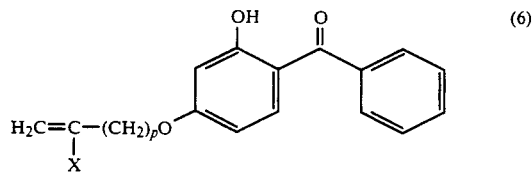

in which X and p have the same meanings as in formula (3).

The platinum catalysts employed for carrying out the hydrosilylation reaction of the polymers of formulae (4) or (5) with the organic derivative of formula (6) are widely described in the literature. It is possible to mention, in particular, the complexes of platinum and of an organic compound described in U.S. Pat. Nos. 3,159,601, 3,159,602, 3,220,972 and European Pat. Nos. EP-A-57,459, EP-A-188,978 and EP-A-190,530, and the complexes of platinum and of vinylated organopolysiloxane, described in U.S. Pat. Nos. 3,419,593, 3,377,432 and 3,814,730.

To react the polymer containing SiH of formula (4) or (5) with the derivative of formula (6), a quantity of platinum catalyst, calculated as the weight of platinum metal, is generally employed, which is between 5 and 600 ppm, preferably between 10 and 200 ppm, based on the weight of polymer containing SiH of formula (4) or (5).

The hydrosilylation reaction may take place in bulk or in a volatile organic solvent such as toluene, heptane, xylene, tetrahydrofuran or tetrachloroethylene, It is generally desirable to heat the reaction mixture to a temperature of 60° to 120° C. for the time needed for the reaction to be complete. The SiH-containing polymer may be added dropwise to the derivative of formula (6) in solution in an organic solvent or the SiH-containing polymer and the derivative of formula (6) may be added simultaneously to a suspension of catalyst in the organic solvent.

A check is made that the reaction is complete by determining the residual SiH groups using alcoholic potassium hydroxide, and the solvent is then removed, for example by distillation under reduced pressure.

The crude oil obtained may be purified, for example, by being passed through a silica absorbent column, Another subject of the invention consists of the cosmetic compositions intended for protecting the skin and the hair from UV radiation, containing an effective quantity of a diorganopolysiloxane containing a 2-hydroxybenzophenone functional group of formula (1) or (2), in a cosmetically acceptable medium.

A further subject of the present invention is a process for protecting the skin and natural or sensitized hair against solar radiation, consisting in applying to the skin or to the hair an effective quantity of at least one compound of formula (1) or (2), contained in a cosmetically acceptable substrate.

"Sensitized hair" means hair which has been subjected to a permanent-waving, dyeing or bleaching treatment.

Another subject of the invention is a coloured or uncoloured composition, stabilized to light, comprising an effective quantity of at least one diorganopolysiloxane containing a 2-hydroxybenzophenone functional group of formula (1) or (2) above.

When employed as a composition intended for protecting human skin against ultraviolet rays, the cosmetic composition according to the invention may be presented in the most diverse forms usually employed for a composition of this type. In particular, it may be presented in the form of oily, alcoholic or oleoalcoholic lotions, of emulsions such as a cream or a milk, of oleoalcoholic, alcoholic or hydroalcoholic gels, of solid sticks, or it may be packaged as an aerosol to form a spray or a foam.

It may contain the cosmetic adjuvants usually employed in a composition of this type, such as thickeners, softeners, humectants, surfactants, preserving agents, antifoams, perfumes, oils, waxes, lanolin, propellants, colorants and/or pigments whose function is to colour the composition itself or the skin, or any other ingredient usually employed in cosmetics.

The compound of formula (1) or (2) is present in proportions by weight of between 0.25 and 3% relative to the total weight of the cosmetic composition for protecting human skin.

The solubilizing solvent employed may be an oil, a wax and, in general terms, any fatty substance, a lower monoalcohol or polyol, a benzoate of $C_{12}$–$C_{15}$ alcohols or mixtures thereof. The more particularly preferred monoalcohols or polyols are ethanol, isopropanol, propylene glycol, hexylene glycol, glycerine and sorbitol.

One embodiment of the invention is an emulsion in the form of protective cream or milk, additionally comprising the compound of formula (1) or (2), fatty alcohols, fatty acid esters and especially fatty acid triglycerides, fatty acids, lanolin, natural or synthetic oil or waxes and emulsifiers, in the presence of water.

Another embodiment consists of oily lotions based on natural or synthetic oils and waxes, lanolin, fatty alcohols and fatty acid esters, especially fatty acid triglycerides, or of oleoalcoholic lotions based on a lower alcohol such as ethanol or a glycol such as propylene glycol and/or a polyol such as glycerine, and oils, waxes and fatty acid esters such as fatty acid triglycerides.

The cosmetic composition of the invention may also be an alcoholic gel comprising one or more lower alcohols or polyols such as ethanol, propylene glycol or glycerine and a thickener such as silica. The oleoalcoholic gels additionally contain a natural or synthetic oil or wax.

The solid sticks consist of natural or synthetic waxes and oils, fatty alcohols, fatty acid esters, lanolin and other fatty substances.

In the case of a composition packaged as an aerosol, conventional propellants such as alkanes, fluoroalkanes and chlorofluoroalkanes are employed.

The present invention also relates to sunscreen cosmetic compositions containing at least one compound of formula (1) or (2) and capable of containing other UV-B and/or UV-A screens.

In this case, the quantity of compound of formula (1) or (2) is between 0.5 and 10% by weight relative to the total weight of the sunscreen composition, the total quantity of screens, if other screens are present, being between 0.5 and 15%.

These sunscreen compositions are in the forms indicated above for the compositions for protecting the human skin.

When the cosmetic composition according to the invention is intended for protecting natural or sensitized hair against UV rays, this composition may be presented in the form of a shampoo, a lotion, foam, gel or emulsion for rinsing, for applying before or after shampooing, before or after dyeing or bleaching or before or after permanent-waving, a hairstyling or conditioning lotion, foam or gel, a lotion, foam or gel for blowdrying or hair setting, a hair-styling spray, or a hair lacquer. Besides the compound of the invention, this composition may contain various adjuvants employed in a composition of this type, such as surface-active agents, thickeners, polymers, softeners, preserving agents, foam stabilizers, electrolytes, organic solvents, silicon derivatives, oils, waxes, defattying agents, colorants and/or pigments whose function is to colour the composition itself or the hair, or any other ingredient usually employed in the field of hair care.

It contains 0.25 to 5% by weight of compound of formula (1) or (2).

The present invention also relates to those cosmetic compositions which include a light-sensitive constituent and contain at least one compound of formula (1) or (2) as an agent for protecting against ultraviolet rays. These compositions consist of hair-care compositions such as hair lacquers, hair setting and optionally conditioning or disentangling lotions, colouring shampoos, hair-dyeing compositions, of makeup products such as nail varnishes, skin-conditioning creams and oils, foundations, lipsticks, skin-care compositions such as bath oils or creams, and any other cosmetic composition which, owing to its constituents, could present problems of light-stability during storage.

Such compositions contain 0.25 to 3% by weight of compound of formula (1) to (2).

The invention also relates to a process for protecting cosmetic compositions against ultraviolet rays, consisting in incorporating in these compositions an effective quantity of at least one compound of formula (1) or (2).

The examples below illustrate the invention without limiting its scope.

EXAMPLES OF PREPARATION

EXAMPLE 1

Preparation of the random polymer of formula:

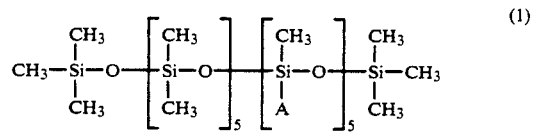

in which A is the residue of formula:

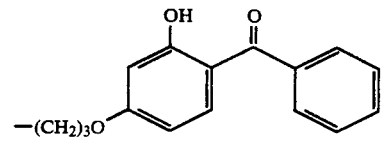

To a suspension of 5% platinum on charcoal (70 mg) in dry toluene (5 ml) at 90°–100° C. is added dropwise over 1 hour 30 minutes, under nitrogen and with stirring, a toluene solution (40 ml) of 4-allyloxy-2-hydroxybenzophenone (12.7 g, 50 meq), prepared according to the process described in Example 1 of U.S. Pat. No. 4,278,804, and of (45–50%)-polymethylhydrodimethylsiloxane copolymer (Petrarch Systems Inc., PS 122.5, 8.13 g, 50 meq as SiH) while the temperature is maintained between 100° and 105° C. Stirring and refluxing are continued until the SiH groups disappear (absence of a band at 2180 cm$^{-1}$ in the infrared), that is for 10 hours. The mixture is filtered through paper, the solvent is removed and the residue is washed three times with 80% ethanol. The oil obtained is taken up in chloroform, is dried over sodium sulphate and is filtered through Celite to remove the colloidal platinum residues. After evaporating off the solvent, a thick pale-yellow oil is obtained.

UV spectrum (CHCl$_3$), $\lambda max_1 = 288$ nm, $\lambda max_2 = 328$ nm.

A nuclear magnetic resonance analysis ($^1$H and Si NMR) shows that this product is indeed the polymer of desired formula.

EXAMPLE 2

Sunscreen oil

| | |
|---|---|
| Compound of Example 1 | 3.5 g |
| Sweet almond oil | 3.0 g |
| Perfume | 1.2 g |
| Benzoate of C$_{12}$/C$_{15}$ alcohols ("Finsolv TN" sold by Witco) | q.s. 100 g |

EXAMPLE 3

Water-in-oil sunscreen emulsion

| | |
|---|---|
| Compound of Example 1 | 3.0 g |
| Mixture of diorganopolysiloxanes and of cetyldimethicone copolyol/cetyldimethicone/polyglyceryl 3-oleate/hexyl laurate/("Abil WS 08" sold by Goldschmidt) emulsifiers | 5.0 g |
| Benzoate of C$_{12}$/C$_{15}$ alcohols ("Finsolv TN" sold Witco) | 12.0 g |
| Vaseline | 2.0 g |
| Beeswax | 2.5 g |
| Glycerine | 2.0 g |
| Sodium chloride | 2.0 g |
| Preserving agent | 0.2 g |
| Perfume | 0.6 g |
| Demineralized water | q.s. 100 g |

EXAMPLE 4

Oil-in-water emulsions for protecting human skin

| | |
|---|---|
| Compound of Example 1 | 1.5 g |
| Mixture of cetylstearyl alcohol and cetylstearyl oxyethylenated with 33 moles of EO ("Sinnowax AO" sold by Henkel) | 7.0 g |
| Glycerol monostearate | 2.0 g |
| Propylene glycol | 10.0 g |
| Cetyl alcohol | 1.3 g |
| Benzoate of C$_{12}$/C$_{15}$ alcohols ("Finsolv TN" sold by Witco) | 15.0 g |
| Preserving agent | 0.2 g |
| Perfume | 0.6 g |
| Demineralized water | q.s. 100 g |

The emulsion of Example 4 is prepared in the following manner:

the fatty substances and the emulsifiers are heated to about 80°-85° C.; the compound of Example 1 is added. The water containing the water-soluble compounds is heated separately to 80°-85° C. and the fatty phase is added to the aqueous phase. After 10 minutes' vigorous stirring, the mixture is allowed to cool with moderate stirring and, at about 40° C., the preserving agent and the perfume are added.

The emulsion of Example 3 is prepared in the same way, except that the aqueous phase is added to the fatty phase.

EXAMPLE 5

Oil for protecting hair

| | |
|---|---|
| Compound of Example 1 | 1 g |
| Oleyl alcohol | 19.5 g |
| Hexylene glycol | 0.5 g |
| Rape oil | q.s. 100 g |

This oil, opalescent in appearance, is applied to dried hair, to which it imparts shine and softness while preserving its colour and its mechanical properties when it is exposed to natural light.

EXAMPLE 6

Protective hair foam

| | |
|---|---|
| Compound of Example 1 | 1 g |
| Nonylphenol oxyethylenated with 10 moles of ethylene oxide, sold under the name of "Montanox 1030" by Sepppic | 10 g |
| Dimethyldialkyl (tallow) ammonium chloride | 0.1 g |
| Water | q.s. 100 g |

This composition is pressurized in an aerosol device in proportions of 90 g of composition to 10 g of propellant, consisting of 3.2N butane.

This composition gives rise to the formation of a foam which is applied to washed and roughly dried hair. It is left for a few minutes and then the hair is rinsed. It disentangles easily and is soft after drying.

EXAMPLE 7

Protective hair cream

| | |
|---|---|
| Compound of Example 1 | 0.5 g |
| Cetylstearyl alcohol oxyethylenated with 33 moles of ethylene oxide | 4 g |
| Cetyl alcohol | 2 g |
| Stearyl alcohol | 2 g |
| Cationic cellulose ether sold under the name "JR400" by Union Carbide | 0.5 g |
| Water | q.s. 100 g |

This emulsion is prepared as in Example 4.

When applied to wet hair, it makes it easy to disentangle. The dried hair is soft and is protected against sun.

We claim:

1. A sunscreening cosmetic composition for screening UV rays with wavelengths of between 280 and 360 nm, which contains, in a cosmetically acceptable vehicle, an effective amount of at least one diorganopolysiloxane having the formula:

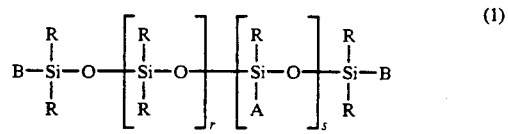

(1)

or the formula

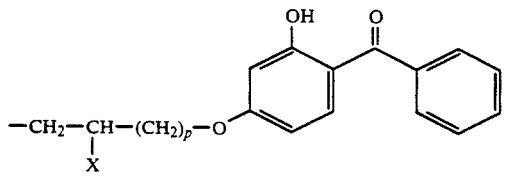

in which formulas:

A is a radical of formula:

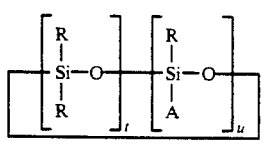

X is hydrogen or linear or branched $C_1$-$C_4$ alkyl, p is an integer between 1 and 10 inclusive, R, which is identical or different, is linear or branched $C_1$-$C_{10}$ alkyl, phenyl, or 3,3,3-trifluoropropyl, at least 80% of R being methyl, B, which is identical or different, is selected from the group consisting of R and A, r is a number between 0 and 200 inclusive, s is a number between 0 and 50 inclusive and if s is 0, at least one of the two symbols B denotes A, u is a number between 1 and 20 inclusive, t is a number between 0 and 20 inclusive, and the sum (t+u) is equal to or greater than 3.

2. A cosmetic composition according to claim 1, which comprises a diorganopolysiloxane of formula (1) or (2), exhibiting at least one of the following characteristics: R is methyl, B is methyl, r is between 5 and 20 inclusive, s is between 2 and 15 inclusive, t+u is between 3 and 10 inclusive, p is equal to 1, X is H or methyl.

3. A cosmetic composition according to claim 1, which comprises a polydimethylsiloxane of formula (1) in which R and B denote methyl, r is equal to 5 and s is equal to 5.

4. A cosmetic composition according to claim 1, which additionally contains cosmetic selected from the group consisting of thickeners, softeners, humectants, surfactants, preserving agents, antifoams, perfumes, oils, waxes, lanolin, lower monoalcohols, polyols, benzoates of $C_{12}$-$C_{15}$ alcohols, propellants, colorants and pigments.

5. A cosmetic composition according to claim 1 which is in the form of an oily, alcoholic or oleoalcoholic lotion, an emulsion, an oleoalcoholic or hydroalcoholic gel, a solid stick, or is packaged as an aerosol to form a spray or a foam.

6. A cosmetic composition according to claim 5 which contains 0.25-3% by weight of diorganopolysiloxane of formula (1) or (2).

7. A cosmetic composition according to claim 5 which may contain other UV-B and/or UV-A screens and contains 0.5-10% by weight of diorganopolysiloxane of formula (1) or (2).

8. A cosmetic composition according to claim 1 which is in the form of a composition for skin care, comprising 0.25-3% by weight of said diorganopolysiloxane.

9. A method for protecting the skin or the hair against ultraviolet radiation with wavelengths of between 280 and 360 nm, which consists in applying thereto an effective quantity of a sunscreening cosmetic composition containing at least one diorganopolysiloxane having the formula:

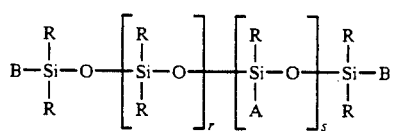

or the formula

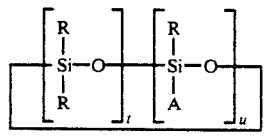

in which formulas:

A is a radical of formula:

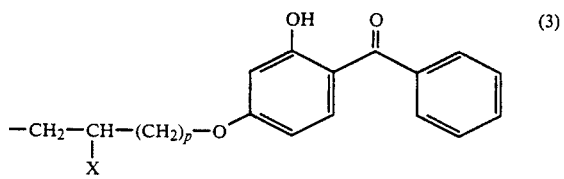

X is hydrogen or linear or branched $C_1$-$C_4$ alkyl, p is an integer between 1 and 10 inclusive, R, which is identical or different, is linear or branched $C_1$-$C_{10}$ alkyl, phenyl, or 3,3,3-trifluoropropyl, at least 80% of R being methyl, B, which is identical or different, is selected from the group consisting of R and A, r is a number between 0 and 200 inclusive, s is a number between 0 and 50 inclusive and if s is 0, at least one of the two symbols B denotes A, u is a number between 1 and 20 inclusive, t is a number between 0 and 20 inclusive, and the sum (t+u) is equal to or greater than 3.

10. A method according to claim 9 in which said diorganopolysiloxane exhibits at least one of the following characteristics: R is methyl, B is methyl, r is between 5 and 20 inclusive, s is between 2 and 15 inclusive, (t+u) is between 3 and 10 inclusive, p is equal to 1, X is H or methyl.

11. A method according to claim 9 in which said composition comprises a polydimethylsiloxane containing 4-allyloxy-2-hydroxybenzophenone grafts of formula (1) in which R and B denote methyl, r is equal to 5 and s is equal to 5.

12. A method for protecting a cosmetic composition against ultraviolet rays with wavelengths of between 280 and 360 nm, which consists in incorporating in said composition an effective quantity of at least one diorganopolysiloxane having the formula:

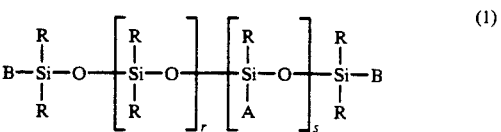

or the formula

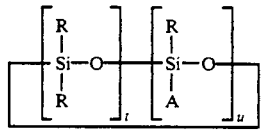

in which formulas:

A is a radical of formula:

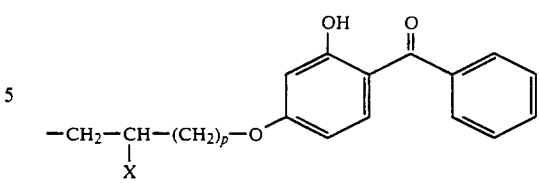

X is hydrogen or linear or branched $C_1$-$C_4$ alkyl,
p is an integer between 1 and 10 inclusive,
R, which is identical or different, is linear or branched $C_1$-$C_{10}$ alkyl, phenyl, or 3,3,3-trifluoropropyl, at least 80% of R being methyl,
B, which is identical or different, is selected from the group consisting of R and A,
r is a number between 0 and 200 inclusive,
s is a number between 0 and 50 inclusive and if s is 0, at least one of the two symbols B denotes A
u is a number between 1 and 20 inclusive,
t is a number between 0 and 20 inclusive, and
the sum (t+u) is equal to or greater than 3.

* * * * *

UNITED STATES PATENT AND TRADEMARK OFFICE
CERTIFICATE OF CORRECTION

PATENT NO. : 5,223,249
DATED : June 29, 1993
INVENTOR(S) : Serge Forestier et al.

It is certified that error appears in the above-indentified patent and that said Letters Patent is hereby corrected as shown below:

Column 1, line 16, "UV-E" should be -- UV-B --.

Column 7, line 11, "Si" should be -- $^{29}Si$ --.

Column 8, line 26, "Sepppic" should be --Seppic--.

Signed and Sealed this

Nineteenth Day of April, 1994

Attest:

BRUCE LEHMAN

*Attesting Officer*     *Commissioner of Patents and Trademarks*